US012690844B2

(12) United States Patent  
Iwasaki et al.

(10) Patent No.: US 12,690,844 B2  
(45) Date of Patent: Jul. 28, 2026

(54) ULTRASOUND DIAGNOSIS APPARATUS AND ULTRASOUND SIGNAL GENERATING METHOD

(71) Applicant: Canon Kabushiki Kaisha, Tokyo (JP)

(72) Inventors: Ryosuke Iwasaki, Otawara (JP); Hiroki Takahashi, Nasushiobara (JP); Tomohisa Imamura, Otawara (JP); Ting Xia, Vernon Hills, IL (US); Liang Cai, Vernon Hills, IL (US); Jian Zhou, Vernon Hills, IL (US); Zhou Yu, Vernon Hills, IL (US)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 18/165,433

(22) Filed: Feb. 7, 2023

(65) Prior Publication Data

US 2024/0260942 A1 Aug. 8, 2024

(51) Int. Cl.  
*A61B 8/00* (2006.01)  
*G01S 7/52* (2006.01)

(52) U.S. Cl.  
CPC ............ *A61B 8/5207* (2013.01); *A61B 8/488* (2013.01); *G01S 7/5206* (2013.01)

(58) Field of Classification Search  
CPC ..... A61B 8/488; A61B 8/5207; A61B 8/5269; G01S 15/8963; G01S 7/52038; G01S 7/5206; G01S 7/52085  
See application file for complete search history.

(56) References Cited

U.S. PATENT DOCUMENTS

| | | | |
|---|---|---|---|
| 6,063,033 A | 5/2000 | Haider et al. | |
| 2016/0166237 A1 | 6/2016 | Yoshiara et al. | |
| 2020/0281570 A1 | 9/2020 | Sato et al. | |
| 2020/0342593 A1 | 10/2020 | Honjo et al. | |

FOREIGN PATENT DOCUMENTS

| | | |
|---|---|---|
| JP | 2003-500150 A | 1/2003 |
| JP | 2016-112400 A | 6/2016 |
| JP | 2020-114293 A | 7/2020 |
| JP | 2020-179029 A | 11/2020 |

*Primary Examiner* — Mark D Remaly  
(74) *Attorney, Agent, or Firm* — Oblon, McClelland, Maier & Neustadt, L.L.P.

(57) ABSTRACT

An ultrasound diagnosis apparatus according to an embodiment includes processing circuitry. This processing circuitry collects a first ultrasound signal including one or more harmonic components. By executing weighed addition processing where a coefficient distribution is applied to the first ultrasound signal for different directions of two or more dimensions, the processing circuitry generates a second ultrasound signal including components of each order at a ratio different, at a specific frequency, from a ratio among the frequency components included in the first ultrasound signal.

6 Claims, 12 Drawing Sheets

68

69

70

ULTRASOUND DIAGNOSIS APPARATUS AND ULTRASOUND SIGNAL GENERATING METHOD

FIELD

Embodiments described herein relate generally to ultrasound diagnosis apparatuses and ultrasound signal generating methods.

BACKGROUND

Tissue harmonic imaging (THI) using harmonic components (non-linear signals) generated in the process of ultrasound propagation has been widely used to obtain ultrasound image data with less artifacts. Second-order harmonic components are normally used, but use of third-order harmonic components has also been proposed. An N-th order (where N is an integer equal to or larger than 2) harmonic component is also referred to simply as an N-th order component or an N-th order harmonic. The phase modulating technique is used to maintain the band of a harmonic component. However, extraction of a third-order harmonic component requires three sets of ultrasound transmission and reception and thus sacrifices the frame rate. To solve this problem, a means has been proposed for inferring data based on a non-linear signal (a harmonic component) from data based on a fundamental signal (a fundamental component) by machine learning.

Because the non-linear signal is generated from the fundamental signal in a trained network used in this machine learning, reproducing a non-linear signal response accurately from a living body is difficult. Furthermore, in a case where a fundamental signal is regarded as a signal obtained by a single set of ultrasound transmission and reception, training performed in obtaining a third-order non-linear signal involves use of: input data that is a fundamental signal obtained by a single set of ultrasound transmission and reception; and target data that is a third-order non-linear signal obtained by three sets of ultrasound transmission and reception. However, the fundamental signal includes a component having a frequency that is an integral multiple of the frequency of the fundamental. That is, the fundamental signal has a complex component. Furthermore, the third-order non-linear signal is obtained by three sets of signal addition. Therefore, the third-order non-linear signal becomes a signal that is more intense than the third-order component included in the fundamental signal by several dB, for example, about 9.5 dB. These signal characteristics reduce the accuracy of the inference of a third-order non-linear signal from a fundamental signal.

DETAILED DESCRIPTION

One of problems to be solved by embodiments disclosed in the specification and drawings is to minimize reduction of frame rates and obtain harmonic components accurately. However, the problems to be solved by the embodiments disclosed in the specification and drawings are not limited to the above mentioned problem. Any problems corresponding to effects due to configurations disclosed through the embodiments described later may be regarded as alternative objects.

An ultrasound diagnosis apparatus according to an embodiment includes processing circuitry. The processing circuitry collects a first ultrasound signal including one or more harmonic components. By executing weighed addition processing, the processing circuitry generates a second ultrasound signal including components of each order at a ratio different, at a specific frequency, from a ratio among the frequency components included in the first ultrasound signal. In this weighted addition processing, a coefficient distribution is applied to the first ultrasound signal for different directions of two or more dimensions.

Ultrasound diagnosis apparatuses and ultrasound signal generating methods according to embodiments and modified examples will hereinafter be described while reference is made to the drawings.

First Embodiment

Figure 1:
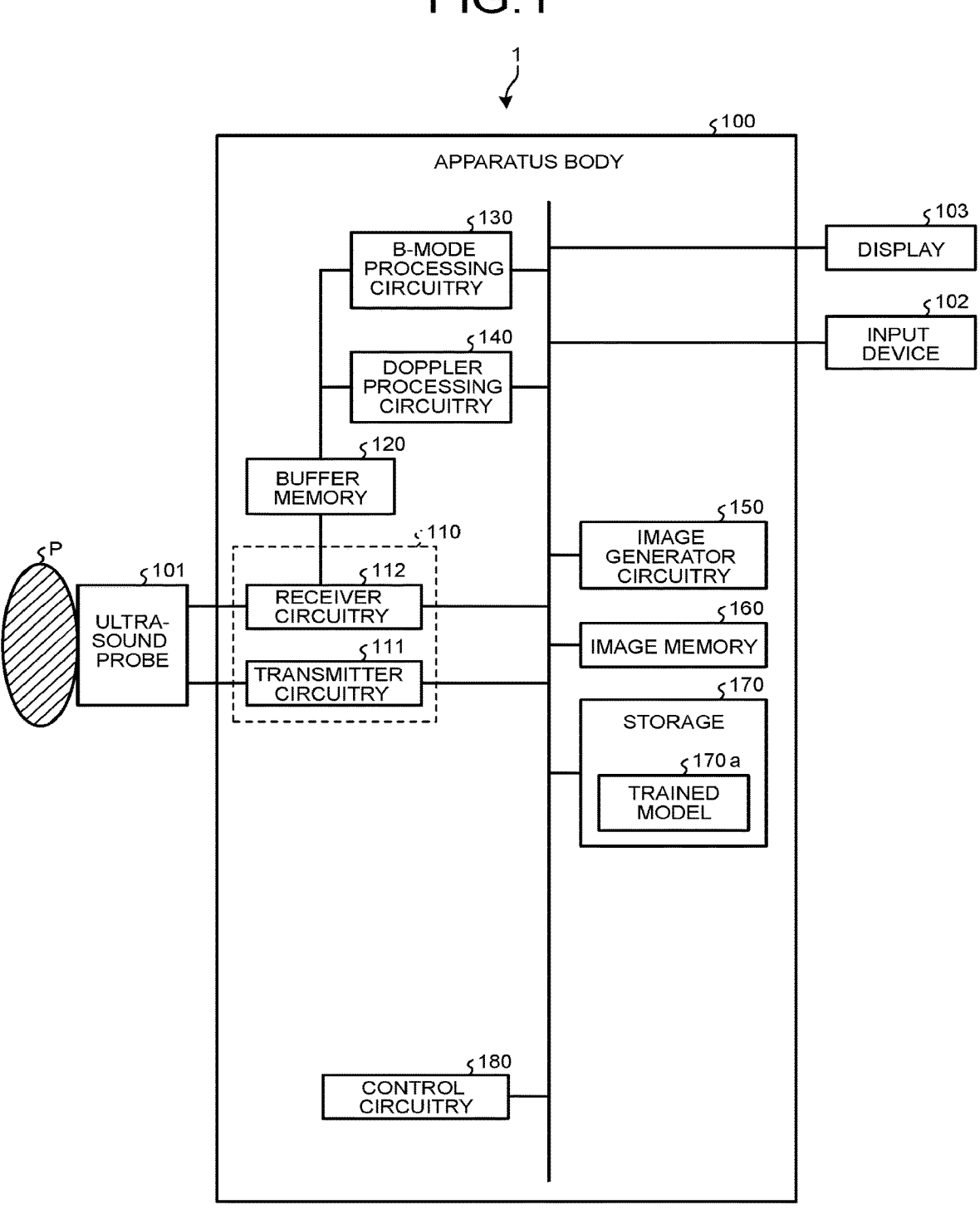
FIG. 1 is a block diagram illustrating an example of a configuration of an ultrasound diagnosis apparatus according to a first embodiment.

FIG. 1 is a block diagram illustrating an example of a configuration of an ultrasound diagnosis apparatus 1 according to a first embodiment. As exemplified by FIG. 1, the ultrasound diagnosis apparatus 1 according to the first embodiment has an apparatus body 100, an ultrasound probe 101, an input device 102, and a display 103.

The ultrasound probe 101 has, for example, plural elements (piezoelectric transducers or piezoelectric elements). These plural elements generate ultrasound on the basis of a drive signal supplied from transmitter circuitry 111 of transmitter and receiver circuitry 110 that the apparatus body 100 has. Specifically, voltage (transmission drive voltage) is applied to the plural elements by the transmitter circuitry 111 and the plural elements thereby generate ultrasound having a waveform according to the transmission drive voltage. The waveform of the transmission drive voltage represented by the drive signal is the waveform of the voltage applied to the plural elements. That is, the ultrasound probe 101 transmits ultrasound according to the magnitude of the transmission drive voltage that has been applied. Furthermore, the ultrasound probe 101 receives reflected waves from a subject P, converts the reflected waves received, into a reflected wave signal that is an electric signal, and outputs the reflected wave signal to the apparatus body 100. The reflected wave signal is an example of an ultrasound signal. Furthermore, the ultrasound probe 101 has, for example, matching layers provided in the elements, and a backing material that prevents backward propagation of ultrasound from the elements. The ultrasound probe 101 is detachably connected to the apparatus body 100.

When ultrasound is transmitted from the ultrasound probe 101 to the subject P, the ultrasound transmitted is: successively reflected by discontinuities in tissue in the body of the subject P, the discontinuities being where the acoustic impedance is discontinuous; and received as reflected waves by the plural elements that the ultrasound probe 101 has. The amplitudes of the reflected waves received are dependent on the acoustic impedance differences at the discontinuities where the ultrasound is reflected. In a case where the transmitted ultrasound pulses are reflected by a surface of a moving body, such as moving blood flow or a moving cardiac wall, frequencies of the reflected waves are shifted dependently on a velocity component of that moving body in the direction the ultrasound is transmitted, due to the Doppler effect. The ultrasound probe 101 outputs the reflected wave signal to receiver circuitry 112 of the transmitter and receiver circuitry 110 described later.

The ultrasound probe 101 is provided to be attachable to and detachable from the apparatus body 100. In a case where scanning (two-dimensional scanning) of a two-dimensional area in the subject P is conducted, an operator connects, for example, the ultrasound probe 101 that is, for example, a 1D array probe having plural elements arranged in a line, to the apparatus body 100. Examples of the 1D array probe include a linear ultrasound probe, a convex ultrasound probe, and a sector ultrasound probe. Furthermore, in a case where scanning (three-dimensional scanning) of a three-dimensional region in the subject P is conducted, an operator connects the ultrasound probe 101 that is, for example, a mechanical 4D probe or a 2D array probe, to the apparatus body 100. The mechanical 4D probe is capable of two-dimensional scanning by use of plural elements arranged in a line like a 1D array probe, and is also capable of three-dimensional scanning by oscillation of plural elements by a predetermined angle (an oscillation angle). Furthermore, the 2D array probe is capable of two-dimensional scanning by means of plural elements arranged in a matrix and through transmission of focused ultrasound.

The input device 102 is implemented by an input means, such as, for example, a mouse, a keyboard, a button, a panel switch, a touch command screen, a foot switch, a trackball, and/or a joystick. The input device 102 receives various setting requests from an operator of the ultrasound diagnosis apparatus 1 and transfers the various setting requests received, to the apparatus body 100.

The display 103 displays a graphical user interface (GUI) for an operator of the ultrasound diagnosis apparatus 1 to input the various setting requests using the input device 102 and displays an ultrasound image based on ultrasound image data generated at the apparatus body 100, for example. The display 103 is implemented by a liquid crystal monitor or an organic light emitting diode (OLED) monitor, for example. The display 103 is an example of a display unit.

On the basis of a reflected wave signal transmitted from the ultrasound probe 101, the apparatus body 100 generates ultrasound image data. The ultrasound image data is an example of an ultrasound signal and also an example of image data. The apparatus body 100 is capable of generating two-dimensional ultrasound image data on the basis of a reflected wave signal corresponding to a two-dimensional area in the subject P, the reflected wave signal having been transmitted from the ultrasound probe 101. Furthermore, the apparatus body 100 is capable of generating three-dimensional ultrasound image data on the basis of a reflected wave signal corresponding to a three-dimensional region in the subject P, the reflected wave signal having been transmitted from the ultrasound probe 101. As illustrated in FIG. 1, the apparatus body 100 has the transmitter and receiver circuitry 110, a buffer memory 120, B-mode processing circuitry 130, Doppler processing circuitry 140, image generator circuitry 150, an image memory 160, a storage 170, and control circuitry 180.

In response to control by the control circuitry 180, the transmitter and receiver circuitry 110 causes ultrasound to be transmitted from the ultrasound probe 101 and causes the ultrasound probe 101 to receive reflected waves of the ultrasound. That is, the transmitter and receiver circuitry 110 executes scanning via the ultrasound probe 101. Scanning may be referred to as a scan, an ultrasound scan, or ultrasound scanning. The transmitter and receiver circuitry 110 is an example of a transmitting and receiving unit. The transmitter and receiver circuitry 110 has the transmitter circuitry 111 and the receiver circuitry 112. The transmitter circuitry 111 is an example of a transmitting unit and the receiver circuitry 112 is an example of a receiving unit.

In response to control by the control circuitry 180, the transmitter circuitry 111 supplies a drive signal to the ultrasound probe 101 and thereby causes the ultrasound probe 101 to transmit ultrasound. The transmitter circuitry 111 has rate pulser circuitry, transmission delay circuitry, and a transmission pulser. In a case where a two-dimensional area in the subject P is to be scanned, the transmitter circuitry 111 causes an ultrasound beam to be transmitted from the ultrasound probe 101, the ultrasound beam being for scanning of the two-dimensional area. Furthermore, in a case where a three-dimensional region in the subject P is to be scanned, the transmitter circuitry 111 causes an ultrasound beam to be transmitted from the ultrasound probe 101, the ultrasound beam being for scanning of the three-dimensional region.

In response to control by the control circuitry 180, the rate pulser circuitry repeatedly generates a rate pulse for forming transmission ultrasound (a transmission beam) at a predetermined pulse repetition frequency (PRF). The rate pulses go through the transmission delay circuitry and voltage is thereby applied to the transmission pulser, in a state of having different transmission delay times. For example, the transmission delay circuitry assigns transmission delay times for the elements to the rate pulses generated by the rate pulser circuitry. These transmission delay times are needed for focusing of ultrasound generated by the ultrasound probe 101 into a beam form and for determination of transmission directivity. The transmission pulser supplies a drive signal (drive pulses) to the ultrasound probe 101 according to the timing based on the rate pulses. That is, the transmission pulser applies voltage (transmission drive voltage) having a waveform represented by the drive signal, to the ultrasound probe 101, according to the timing based on the rate pulses. By changing the transmission delay times assigned to the rate pulses, the transmission delay circuitry freely adjusts the direction in which the ultrasound is transmitted from surfaces of the elements.

At the elements in the ultrasound probe 101, the drive pulses are converted into mechanical vibration from the electric signal, after being transmitted to the elements via a cable from the transmission pulser. That is, by application of voltage to the elements, the elements vibrate mechanically. Ultrasound generated by this mechanical vibration is transmitted into a living body (inside the subject P). Ultrasound having different transmission delay times for the elements is focused and propagates in a predetermined direction.

The transmitter circuitry 111 has a function of being capable of instantly changing transmission frequency and transmission drive voltage, for example, to execute a predetermined scanning sequence in response to control by the control circuitry 180. In particular, changing the transmission drive voltage is implemented by linear amplifier transmitter circuitry capable of instantaneously changing the value of transmission drive voltage, or a mechanism that electrically switches between plural power supply units. The transmission frequency is, for example, the center frequency of ultrasound that is transmitted.

After reaching the elements inside the ultrasound probe 101, reflected waves of ultrasound transmitted by the ultrasound probe 101 are converted, at the elements, into an electric signal (a reflected wave signal) from mechanical vibration and the reflected wave signal is input to the receiver circuitry 112. The receiver circuitry 112 has a pre-amplifier, an analog to digital (A/D) converter, and quadrature detection circuitry, for example, and generates reflected wave data by performing various kinds of processing of the reflected wave signal transmitted from the ultrasound probe 101. The receiver circuitry 112 stores the reflected wave data generated, into the buffer memory 120. The reflected wave data is an example of an ultrasound signal.

The pre-amplifier performs gain adjustment (gain correction) by amplifying the reflected wave signal for each channel. The A/D converter converts the gain-corrected reflected wave signal into a digital signal by A/D conversion of the gain-corrected reflected wave signal. The quadrature detection circuitry converts the reflected wave signal that has been converted into the digital signal, into an in-phase signal (I signal) and a quadrature-phase signal (Q signal) of a baseband. The quadrature detection circuitry then stores the I signal and Q signal (IQ signals) as reflected wave data, into the buffer memory 120.

The receiver circuitry 112 generates two-dimensional reflected wave data from a two-dimensional reflected wave signal transmitted from the ultrasound probe 101. Furthermore, the receiver circuitry 112 generates three-dimensional reflected wave data from a three-dimensional reflected wave signal transmitted from the ultrasound probe 101.

In this embodiment, the ultrasound diagnosis apparatus 1 is capable of performing various types of processing in real time. For example, the ultrasound probe 101 transmits a reflected wave signal corresponding to one frame, one after another, to the receiver circuitry 112. Every time the receiver circuitry 112 receives a reflected wave signal corresponding to one frame transmitted from the ultrasound probe 101, the receiver circuitry 112 generates reflected wave data corresponding to that one frame from the reflected wave signal corresponding to that one frame. Every time the receiver circuitry 112 generates reflected wave data of one frame, the receiver circuitry 112 stores the reflected data corresponding to that one frame into the buffer memory 120.

The buffer memory 120 is a memory that temporarily stores reflected wave data generated by the transmitter and receiver circuitry 110. For example, the buffer memory 120 is configured to be capable of storing reflected wave data corresponding to a predetermined number of frames. In a case where reflected wave data of one frame is newly generated by the receiver circuitry 112 in a state where the buffer memory 120 has stored reflected wave data corresponding to the predetermined number of frames, the buffer memory 120 discards, in response to control by the receiver circuitry 112, the reflected wave data of one frame that was generated at the earliest time and stores the newly generated reflected wave data of one frame. For example, the buffer memory 120 is implemented by a semiconductor memory device, such as a random access memory (RAM) or a flash memory.

The B-mode processing circuitry 130 reads reflected wave data from the buffer memory 120, performs various types of signal processing of the reflected wave data read, and outputs, as B-mode data, the reflected wave data that have been subjected to the various types of signal processing, to the image generator circuitry 150. The B-mode processing circuitry 130 is implemented by, for example, a processor. The B-mode processing circuitry 130 is an example of a B-mode processing unit. Furthermore, the B-mode data is an example of an ultrasound signal.

For example, every time reflected wave data of one frame is newly stored into the buffer memory 120, the B-mode processing circuitry 130 reads the reflected wave data of one frame newly stored in the buffer memory 120. By performing various types of signal processing of the read reflected wave data of one frame, the B-mode processing circuitry 130 newly generates B-mode data of that one frame. Every time the B-mode processing circuitry 130 generates B-mode data of one frame, the B-mode processing circuitry 130 outputs the newly generated B-mode data of one frame, to the image generator circuitry 150. An example of the various types of signal processing executed by the B-mode processing circuitry 130 will be described hereinafter.

For example, the B-mode processing circuitry 130 subjects reflected wave data read from the buffer memory 120, to quadrature detection and then logarithmic amplification and envelope detection processing, for example, to generate B-mode data having sample points with signal intensities (amplitude intensities) represented by brightness. The B-mode processing circuitry 130 then outputs the B-mode data generated, to the image generator circuitry 150.

The Doppler processing circuitry 140 reads reflected wave data from the buffer memory 120, performs various types of signal processing of the reflected wave data read, and outputs, as Doppler data, the reflected wave data that have been subjected to the various types of signal processing, to the image generator circuitry 150. The Doppler processing circuitry 140 is implemented by, for example, a processor. The Doppler processing circuitry 140 is an example of a Doppler processing unit.

For example, every time reflected wave data of one frame is newly stored into the buffer memory 120, the Doppler processing circuitry 140 reads the reflected wave data of one frame newly stored in the buffer memory 120. By performing various types of signal processing of the read reflected wave data of one frame, the Doppler processing circuitry 140 newly generates B-mode data of that one frame. Every time the Doppler processing circuitry 140 generates Doppler data of one frame, the Doppler processing circuitry 140 outputs the newly generated Doppler data of one frame, to the image generator circuitry 150. An example of the various types of signal processing executed by the Doppler processing circuitry 140 will be described hereinafter.

For example, by performing frequency analysis of reflected wave data read from the buffer memory 120, the Doppler processing circuitry 140 extracts movement information on a moving body (for example, blood flow, tissue, or a contrast agent echo component) based on the Doppler effect, from the reflected wave data, and generates Doppler data representing the movement information extracted. For example, the Doppler processing circuitry 140 extracts, as the movement information on the moving body, for example, the mean velocity, the mean variance value, and the mean power value, from multiple points, and generates Doppler data representing the extracted movement information on the moving body. The Doppler processing circuitry 140 outputs the Doppler data generated, to the image generator circuitry 150.

The ultrasound diagnosis apparatus 1 is capable of executing the color Doppler method also referred to as the color flow mapping (CFM) method, by using the above described functions of the Doppler processing circuitry 140. In this color flow mapping method, ultrasound transmission and reception are performed a plural number of times on plural scan lines. In the color flow mapping method, by passing data strings for the same position through a moving target indicator (MTI) filter, a signal originating from still tissue or slowly moving tissue (a clutter signal) is suppressed and a signal originating from blood flow (a blood flow signal) is extracted. In the color flow mapping method, pieces of blood flow information, such as the velocity (the mean velocity) of blood flow, the variance of blood flow (the mean variance value), and the power of blood flow (the mean power value), are estimated from the blood flow signal. The Doppler processing circuitry 140 outputs color Doppler data representing the blood flow information estimated by the color flow mapping method, to the image generator circuitry 150. The color Doppler data is an example of Doppler data.

The B-mode processing circuitry 130 and the Doppler processing circuitry 140 are capable of processing both two-dimensional reflected wave data and three-dimensional reflected wave data.

The image generator circuitry 150 generates various ultrasound image data from B-mode data output from the B-mode processing circuitry 130 or Doppler data output from the Doppler processing circuitry 140. The image generator circuitry 150 is implemented by a processor.

For example, the image generator circuitry 150 generates, from two-dimensional B-mode data generated by the B-mode processing circuitry 130, two-dimensional B-mode image data representing the intensity of reflected waves by brightness. Furthermore, the image generator circuitry 150 generates two-dimensional Doppler image data or two-dimensional color image data having imaged movement information or blood flow information, from two-dimensional Doppler data or Doppler color data generated by the Doppler processing circuitry 140. The two-dimensional Doppler image data having the imaged movement information or the two-dimensional color image data having the imaged blood flow information is velocity image data, variance image data, power image data, or any combination of these image data.

Typically, the image generator circuitry 150 generates ultrasound image data for display by converting (scan-converting) scan line signal strings from ultrasound scanning, into scan line signal strings having a video format typical of television, for example. For example, the image generator circuitry 150 generates ultrasound image data for display by performing coordinate transformation of data output from the B-mode processing circuitry 130 and the Doppler processing circuitry 140, according to the ultrasound scan mode of the ultrasound probe 101. Furthermore, the image generator circuitry 150 may perform various types of image processing other than the scan-converting, by using plural image frames that have been scan-converted, the various types of image processing including, for example, image processing (smoothing processing) for regenerating a mean value image for brightness and image processing (edge enhancement processing) using a differential filter in the image. In addition, the image generator circuitry 150 may also combine the ultrasound image data with textual information on various parameters, scales, and body marks, for example.

Furthermore, by performing coordinate transformation of three-dimensional B-mode data generated by the B-mode processing circuitry 130, the image generator circuitry 150 generates three-dimensional B-mode image data. In addition, by performing coordinate transformation of three-dimensional Doppler data generated by the Doppler processing circuitry 140, the image generator circuitry 150 generates three-dimensional Doppler image data. That is, the image generator circuitry 150 generates, as "three-dimensional ultrasound image data (volume data)", "three-dimensional B-mode image data and three-dimensional Doppler image data". The image generator circuitry 150 then performs various types of rendering processing of the volume data to generate various two-dimensional image data for displaying the volume data on the display 103.

The rendering processing performed by the image generator circuitry 150 may include, for example, processing of generating multiplanar reconstruction (MPR) image data from the volume data using MPR. Furthermore, the rendering processing performed by the image generator circuitry 150 may include, for example, volume rendering (VR) processing of generating two-dimensional image data reflecting three-dimensional information. The image generator circuitry 150 is an example of an image generating unit.

B-mode data and Doppler data are ultrasound image data that has not been subjected to scan-converting yet, and data generated by the image generator circuitry 150 is ultrasound image data for display that has been scan-converted. The B-mode data and Doppler data are also referred to as raw data.

The image memory 160 is a memory that stores various image data generated by the image generator circuitry 150. Furthermore, the image memory 160 stores data generated by the B-mode processing circuitry 130 and the Doppler processing circuitry 140. B-mode data and Doppler data stored in the image memory 160 are, for example, able to be called by an operator after diagnosis, and formed into ultrasound image data for display via the image generator circuitry 150. For example, the image memory 160 is implemented by: a semiconductor memory device, such as a random access memory (RAM) or a flash memory; a hard disk; or an optical disk.

The storage 170 stores: a control program for performing scanning (ultrasound transmission and reception), image processing, and display processing; and various data, such as diagnostic information (for example, patient IDs and observations by doctors), diagnostic protocols, and various body marks. Furthermore, the storage 170 is used, as required, for storage of data stored in the image memory 160, for example. For example, the storage 170 is implemented by: a semiconductor memory device, such as a flash memory; a hard disk; or an optical disk.

Furthermore, the storage 170 according to this embodiment stores a trained model 170a. The storage 170 may have the trained model 170a stored already at the time of delivery of the ultrasound diagnosis apparatus 1, or the trained model 170a obtained from an external device, for example, after the delivery of the ultrasound diagnosis apparatus 1, may be stored in the storage 170. This trained model 170a will be described later.

The control circuitry 180 controls the overall processing by the ultrasound diagnosis apparatus 1. Specifically, the control circuitry 180 controls the processing by the transmitter circuitry 111, the receiver circuitry 112, the B-mode processing circuitry 130, the Doppler processing circuitry 140, and the image generator circuitry 150, on the basis of various setting requests input by an operator via the input device 102 and various control programs and various data read from the storage 170. Furthermore, the control circuitry 180 controls the display 103 to display an ultrasound image based on ultrasound image data for display stored in the image memory 160. For example, the control circuitry 180 controls the display 103 to display a B-mode image based on B-mode image data, or a color image based on color image data. Furthermore, the control circuitry 180 controls the display 103 to display a color image superimposed on a B-mode image. The control circuitry 180 is an example of a display control unit or a control unit. The control circuitry 180 is implemented by, for example, a processor.

Furthermore, by controlling the ultrasound probe 101 via the transmitter and receiver circuitry 110, the control circuitry 180 controls ultrasound scanning.

The term, "processor", used in the description means, for example, a circuit, such as a central processing unit (CPU), a graphics processing unit (GPU), an application specific integrated circuit (ASIC), or a programmable logic device (for example, a simple programmable logic device (SPLD), a complex programmable logic device (CPLD), or a field programmable gate array (FPGA)). A processor implements a function by reading a program stored in the storage 170 and executing the program read. Instead of being stored in the storage 170, the program may be directly incorporated in a circuit of the processor. In this case, by reading and executing the program incorporated in the circuit, the processor implements the function. Each of the processors according to the embodiment is not necessarily configured as a single circuit, and plural independent circuits may be combined together to be configured as a single processor to implement their functions. Furthermore, plural pieces of circuitry in FIG. 1 (for example, the B-mode processing circuitry 130, the Doppler processing circuitry 140, the image generator circuitry 150, and the control circuitry 180) may be integrated into a single processor to implement their functions. That is, the B-mode processing circuitry 130, the Doppler processing circuitry 140, the image generator circuitry 150, and the control circuitry 180 may be integrated into a single piece of processing circuitry implemented by a processor. The transmitter and receiver circuitry 110, the B-mode processing circuitry 130, the Doppler processing circuitry 140, the image generator circuitry 150, and the control circuitry 180 may be integrated into a single piece of processing circuitry including a processor.

The overall configuration of the ultrasound diagnosis apparatus 1 according to the first embodiment has been described hereinbefore. The ultrasound diagnosis apparatus 1 configured as described above executes processing described hereinafter, to enable both: minimization of reduction in the frame rate; and accurate obtainment of a harmonic component.

Figure 2:
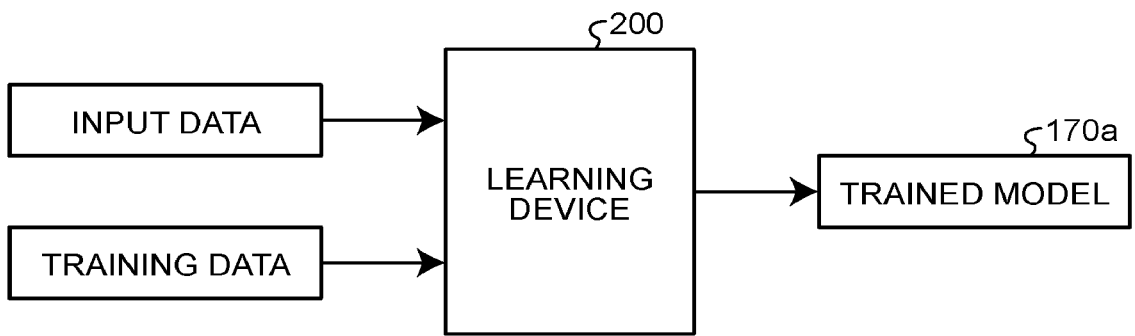
FIG. 2 is a diagram for explanation of an example of a method of generating a trained model, according to the first embodiment.

FIG. 2 is a diagram for explanation of an example of a method of generating the trained model 170a, according to the first embodiment. The trained model 170a is a machine learning model that has been trained, the machine learning model having been obtained by causing a machine learning model to perform machine learning, on the basis of input data and target data, according to a model learning program. The trained model 170a is generated by a learning device 200.

The learning device 200 includes a machine learning model, such as a convolution neural network (CNN). The learning device 200 generates the trained model 170a by performing learning (supervised learning) based on input data and target data related to ultrasound examination of the same position (the same cross section of the same site) in a subject. The trained model 170a has a function of outputting data (output data) corresponding to the target data in response to input of data corresponding to the input data, when making an inference. The ultrasound diagnosis apparatus 1 may include a function similar to the function of the learning device 200 and the ultrasound diagnosis apparatus 1 may, instead of the learning device 200, generate the trained model 170a.

The following description is on a case where the machine learning model is a CNN. In this case, the input data is input to the CNN that is the machine learning model in the learning device 200. By applying the CNN to the input data, the learning device 200 generates the output data. The output data is then output from the CNN. The output data is input to an evaluating function in the learning device 200. Furthermore, the target data is also input to the evaluating function. By means of the evaluating function, the learning device 200 evaluates: the output data that is generated in the CNN on the basis of the input data; and the target data. The evaluating function compares the generated output data with the target data, for example, and corrects coefficients of the CNN (network parameters, such as weight and bias) by backpropagation. Evaluation by the evaluating function is fed back to the CNN. The learning device 200 repeats such supervised learning based on input data and target data obtained for the same position in a subject until the error between the output data and the target data becomes equal to or less than a predetermined threshold, for example. The learning device 200 is capable of outputting the trained machine learning model as the trained model 170a.

For example, coefficients are generated in the CNN, the coefficients allowing features of input data to be converted into target data in response to input of the input data and the target data. The greater the numbers of input data and target data used in machine learning, the better, and for example, the number of data is preferably several thousands or more.

Figure 3:
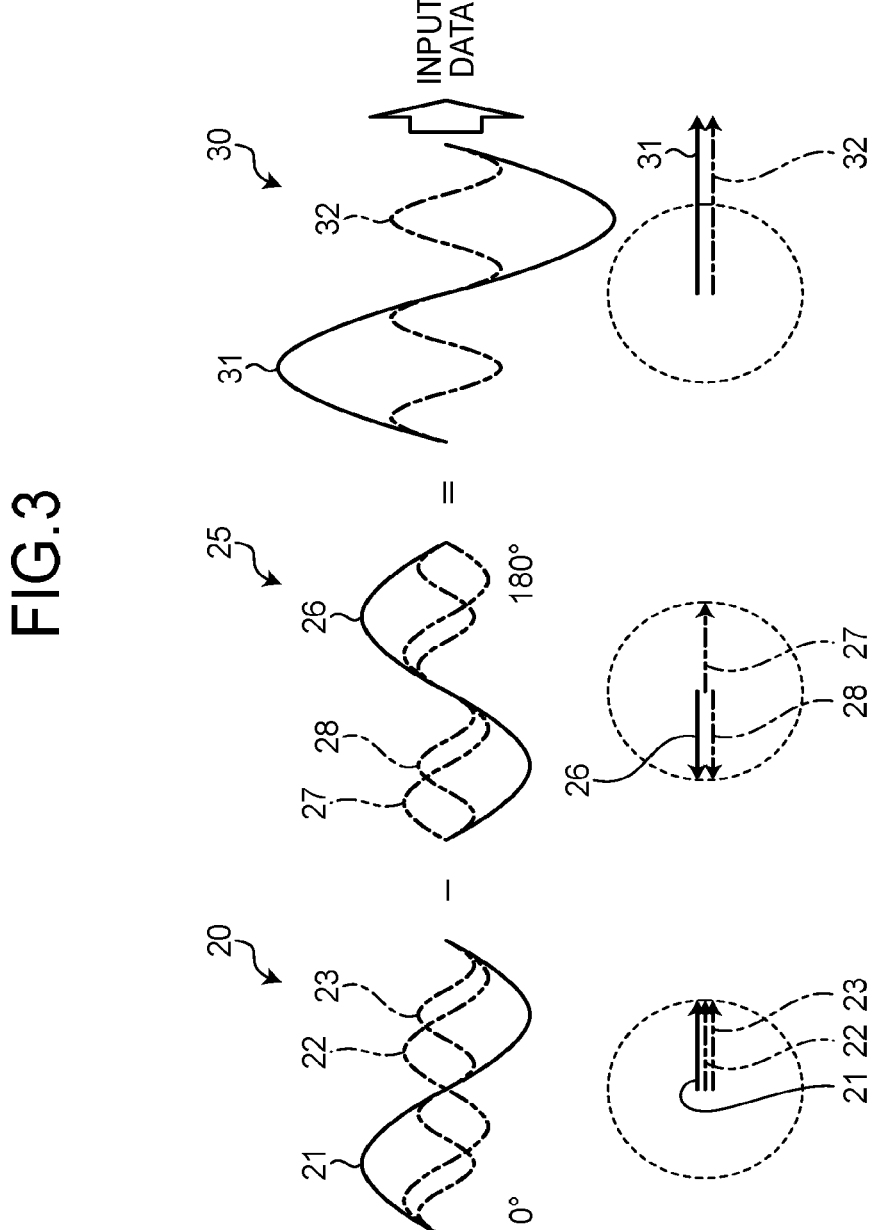
FIG. 3 is a diagram for explanation of an example of a method of generating input data, according to the first embodiment.
Figure 4:
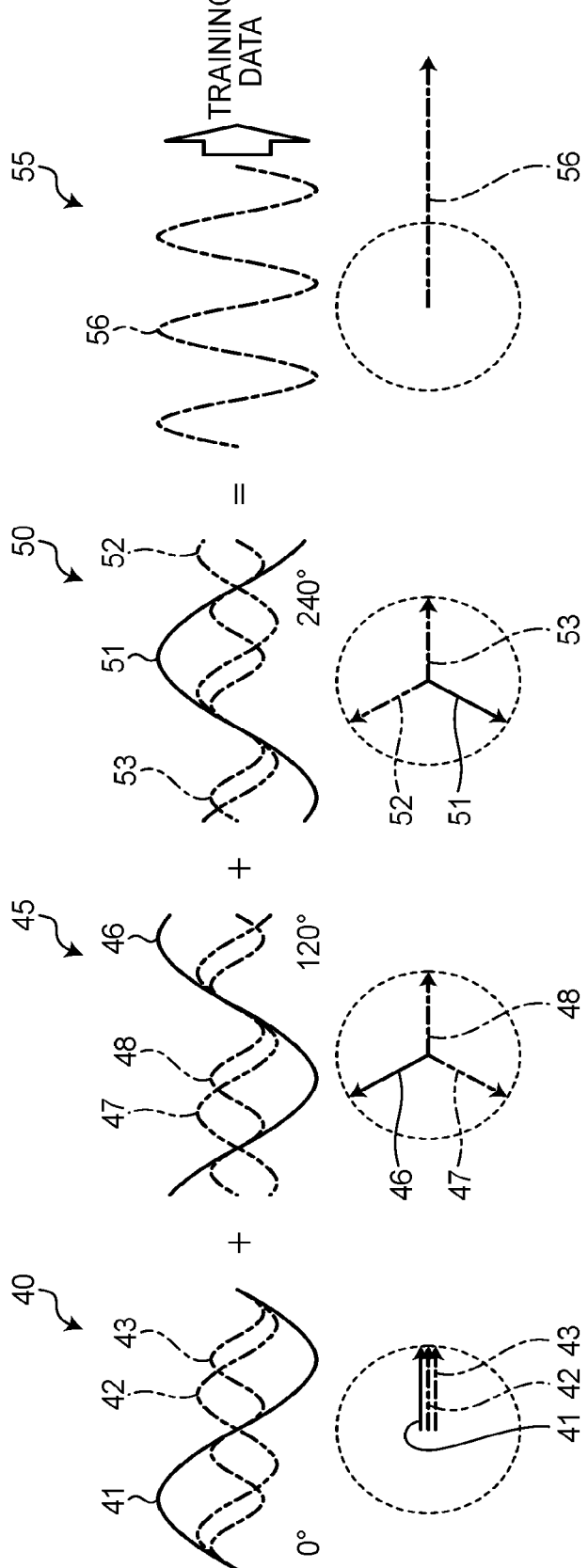
FIG. 4 is a diagram for explanation of an example of a method of generating target data, according to the first embodiment.

A method of generating input data and target data used in machine learning at the learning device 200 will be described by reference to FIG. 3 and FIG. 4. FIG. 3 is a diagram for explanation of an example of a method of generating input data, according to the first embodiment. FIG. 4 is a diagram for explanation of an example of a method of generating target data, according to the first embodiment.

As illustrated in FIG. 3, the input data is an ultrasound signal 30 obtained by subtraction of an ultrasound signal 25 from an ultrasound signal 20. The ultrasound signal 20 and the ultrasound signal 25 are obtained by ultrasound transmission and reception performed twice by the ultrasound diagnosis apparatus 1. With respect to this first embodiment, a case where the ultrasound signal 20 and the ultrasound signal 25 are reflected wave data obtained by the receiver circuitry 112 will be described hereinafter.

The center frequency (the frequency of the fundamental) included in the ultrasound transmitted for the first time and the center frequency included in the ultrasound transmitted for the second time are the same. However, the phase of the center frequency included in the ultrasound transmitted for the first time and the phase of the center frequency included in the ultrasound transmitted for the second time differ from each other by 180 degrees. Furthermore, the position in the subject P, the position being where the ultrasound is transmitted to for the first time, and the position in the subject P, the position being where the ultrasound is transmitted to for the second time, are the same. That is, the scanned region in the subject P scanned by the first ultrasound transmission and reception and the scanned region in the subject P scanned by the second ultrasound transmission and reception are the same.

For example, in the first ultrasound transmission and reception, the ultrasound probe 101 transmits transmission ultrasound having a center frequency with a phase of 0 degrees to a predetermined position in the subject P, receives reflected waves from the subject P, and transmits a reflected wave signal to an apparatus body 10. This reflected wave signal includes harmonic components not included in the transmission ultrasound, because the subject P has non-linear characteristics.

In this first embodiment, it is assumed that the frequency corresponding to any harmonic component of the fourth-order or higher is not included in the reception band of the ultrasound probe 101. Therefore, a reflected wave signal output from the ultrasound probe 101 includes, in addition to a fundamental component, a first-order harmonic component, a second-order harmonic component, and a third-order harmonic component, but does not include any harmonic component of the fourth order or higher.

For example, as illustrated in FIG. 3, the ultrasound signal 20 obtained by the first ultrasound transmission and reception includes a fundamental component 21, a second-order harmonic component 22, and a third-order harmonic component 23.

Furthermore, for example, in the second ultrasound transmission and reception, the ultrasound probe 101 transmits transmission ultrasound having a center frequency with a phase of 180 degrees to the predetermined position in the subject P, receives reflected waves from the subject P, and transmits a reflected wave signal to the apparatus body 10. The ultrasound signal 25 obtained by the second ultrasound transmission and reception includes a fundamental component 26, a second-order harmonic component 27, and a third-order harmonic component 28.

As illustrated in FIG. 3, the phase corresponding to the fundamental component 21 and the phase corresponding to the fundamental component 26 differ from each other by 180 degrees. Furthermore, the phase corresponding to the third-order harmonic component 23 and the phase corresponding to the third-order harmonic component 28 differ from each other by 180 degrees. However, the phase corresponding to the second-order harmonic component 22 and the phase corresponding to the second-order harmonic component 27 are the same.

Therefore, the ultrasound signal 30 includes a fundamental component 31 and a third-order harmonic component 32, and does not include any second-order harmonic component. That is, the ultrasound signal 30 is a signal having a fundamental component and a third-order harmonic component that have been enhanced, and a second-order harmonic component in the signal has been suppressed.

The learning device 200 is connected to the ultrasound diagnosis apparatus 1, obtains the ultrasound signal 20 and the ultrasound signal 25 from the ultrasound diagnosis apparatus 1, subtracts the ultrasound signal 25 from the ultrasound signal 20 to generate the ultrasound signal 30, and uses the ultrasound signal 30 generated, as input data. The learning device 200 may obtain the ultrasound signal 30 generated by the ultrasound diagnosis apparatus 1 and use the ultrasound signal 30 obtained, as input data.

Furthermore, as illustrated in FIG. 4, target data is an ultrasound signal 55 obtained by adding up an ultrasound signal 40, an ultrasound signal 45, and an ultrasound signal 50. The ultrasound signal 40, the ultrasound signal 45, and the ultrasound signal 50 are obtained by ultrasound transmission and reception performed three times by the ultrasound diagnosis apparatus 1. With respect to this first embodiment, a case where the ultrasound signal 40, the ultrasound signal 45, and the ultrasound signal 50 are reflected wave data obtained by the receiver circuitry 112 will be described hereinafter.

The center frequency included in the ultrasound transmitted for the first time, the center frequency included in the ultrasound transmitted for the second time, and the center frequency included in the ultrasound transmitted for the third time are the same. However, the phase of the center frequency included in the ultrasound transmitted for the first time and the phase of the center frequency included in the ultrasound transmitted for the second time differ from each other by 120 degrees. Furthermore, the phase of the center frequency included in the ultrasound transmitted for the first time and the phase of the center frequency included in the ultrasound transmitted for the third time differ from each other by 240 degrees.

Furthermore, the subject P to which ultrasound is transmitted for generation of input data and the subject P to which ultrasound is transmitted for generation of target data are the same. In addition, the position in the subject P where the ultrasound is transmitted to for the generation of input data and the position in the subject P where the ultrasound is transmitted to for the generation of target data are the same. That is, the scanned region in the subject P for the generation of input data and the scanned region in the subject P for the generation of target data are the same.

Furthermore, the position in the subject P, the position being where the ultrasound is transmitted to for the first time; the position in the subject P, the position being where the ultrasound is transmitted to for the second time; and the position in the subject, the position being where the ultrasound is transmitted to for the third time, are the same. That is, the scanned region in the subject P scanned by the first ultrasound transmission and reception, the scanned region in the subject P scanned by the second ultrasound transmission and reception, and the scanned region in the subject P scanned by the third ultrasound transmission and reception are the same.

For example, in the first ultrasound transmission and reception, the ultrasound probe 101 transmits transmission ultrasound having a center frequency with a phase of 0 degrees to the predetermined position in the subject P, receives reflected waves from the subject P, and transmits a reflected wave signal to the apparatus body 10. The ultrasound signal 40 obtained by the first ultrasound transmission and reception includes a fundamental component 41, a second-order harmonic component 42, and a third-order harmonic component 43.

Furthermore, for example, in the second ultrasound transmission and reception, the ultrasound probe 101 transmits transmission ultrasound having a center frequency with a phase of 120 degrees to the predetermined position in the subject P, receives reflected waves from the subject P, and transmits a reflected wave signal to the apparatus body 10. The ultrasound signal 45 obtained by the second ultrasound transmission and reception includes a fundamental component 46, a second-order harmonic component 47, and a third-order harmonic component 48.

Furthermore, for example, in the third ultrasound transmission and reception, the ultrasound probe 101 transmits transmission ultrasound having a center frequency with a phase of 240 degrees to the predetermined position in the subject P, receives reflected waves from the subject P, and transmits a reflected wave signal to the apparatus body 10. The ultrasound signal 50 obtained by the third ultrasound transmission and reception includes a fundamental component 51, a second-order harmonic component 52, and a third-order harmonic component 53.

As illustrated in FIG. 4, the phase corresponding to the fundamental component 41, the phase corresponding to the fundamental component 46, and the phase corresponding to the fundamental component 51 differ from each other by 120 degrees. Furthermore, the phase corresponding to the second-order harmonic component 42, the phase corresponding to the second-order harmonic component 47, and the phase corresponding to the second-order harmonic component 52 differ from each other by 120 degrees. However, the phase corresponding to the third-order harmonic component 43, the phase corresponding to the third-order harmonic component 48, and the phase corresponding to the third-order harmonic component 53 are the same.

Therefore, the ultrasound signal 55 includes a third-order harmonic component 56 and does not include any fundamental component and second-order harmonic component. That is, the ultrasound signal 55 is a signal having a third-order harmonic component that has been enhanced, and a fundamental component and a second-order harmonic component in the signal have been suppressed.

The learning device 200 obtains the ultrasound signal 40, the ultrasound signal 45, and the ultrasound signal 50 from the ultrasound diagnosis apparatus 1, adds up the ultrasound signal 40, the ultrasound signal 45, and the ultrasound signal 50 to generate the ultrasound signal 55, and uses the ultrasound signal 55 generated, as target data. The learning device 200 may obtain the ultrasound signal 55 generated by the ultrasound diagnosis apparatus 1 and use the ultrasound signal 50 obtained, as target data.

The learning device 200 generates the trained model 170a by using input data (the ultrasound signal 30) and target data (the ultrasound signal 55) generated by the method described above. The learning device 200 generates the trained model 170a for each site to be scanned. The ultrasound diagnosis apparatus 1 then obtains the trained model 170a generated for each site, from the learning device 200, and stores the obtained trained model 170a for each site, into the storage 170. In making an inference, the ultrasound diagnosis apparatus 1 obtains the trained model 170a corresponding to a site to be scanned, from the storage 170, infers output data corresponding to input data by using the trained model 170a obtained, and outputs the output data inferred.

For example, the trained model 170a generated by the learning device 200 is implemented by the CNN described above. In this case, in making an inference, the trained model 170a generates output data by performing, on input data, convolution processing using a filter having a predetermined kernel size and deconvolution processing using a filter having a predetermined kernel size, and outputs the output data generated.

Figure 5:
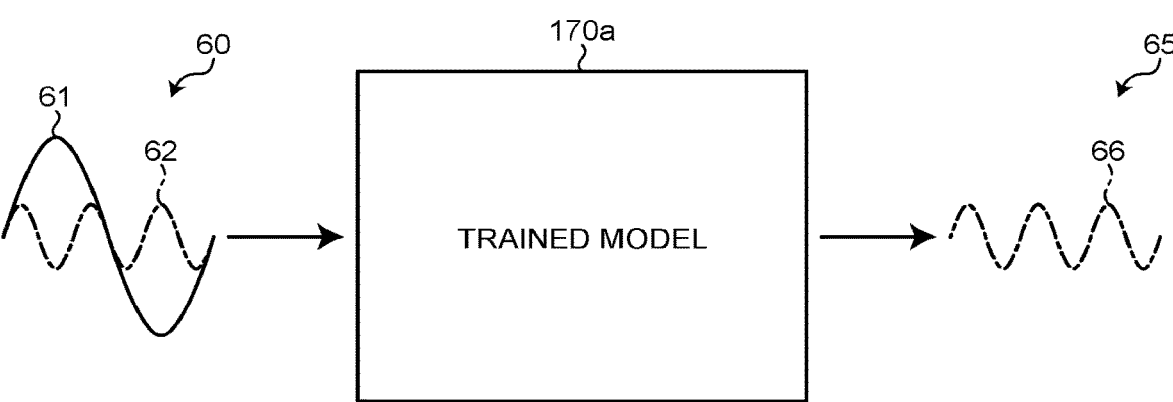
FIG. 5 is a diagram for explanation of an example of operation in inference by the trained model, according to the first embodiment.

FIG. 5 is a diagram for explanation of an example of operation in inference by the trained model 170a, according to the first embodiment. The receiver circuitry 112 of the ultrasound diagnosis apparatus 1 generates an ultrasound signal 60, as illustrated in FIG. 5. That is, the ultrasound probe 101, and the transmitter and receiver circuitry 110 collect the ultrasound signal 60 including two different components that are a fundamental component and a harmonic component. The ultrasound signal 60 thus includes a fundamental component and at least one harmonic component. Furthermore, the ultrasound signal 60 includes two different frequency components. The ultrasound probe 101, and the transmitter and receiver circuitry 110 thus have a function of collecting the ultrasound signal 60 and is an example of a collecting unit. The ultrasound signal 60 is an example of a first ultrasound signal.

Furthermore, the receiver circuitry 112 obtains the trained model 170a corresponding to a site to be scanned, from the trained models 170a stored in the storage 170, the trained models 170a corresponding to the respective sites. The receiver circuitry 112 then inputs the ultrasound signal 60 generated, into the trained model 170a. The ultrasound signal 60 is generated by a method similar to the method of generating the ultrasound signal 30 illustrated in FIG. 3. That is, upon inference, the ultrasound diagnosis apparatus 1 performs ultrasound transmission and reception twice, and the receiver circuitry 112 generates the ultrasound signal 60 by subtracting the ultrasound signal (reflected wave data) obtained by the second ultrasound transmission and reception from the ultrasound signal (reflected wave data) obtained by the first ultrasound transmission and reception.

In other words, in the inference: the ultrasound diagnosis apparatus 1 performs ultrasound transmission twice; the phase of the center frequency of the ultrasound transmitted in the first ultrasound transmission is different from the phase of the center frequency of the ultrasound transmitted in the second ultrasound transmission; and the ultrasound diagnosis apparatus 1 generates the ultrasound signal 60 by subtracting, from one of plural (two) ultrasound signals obtained by the ultrasound transmission performed twice, the other ultrasound signal obtained by the second ultrasound transmission and reception, the one being the ultrasound signal obtained by the first ultrasound transmission and reception. The phase of the center frequency of the ultrasound transmitted for the first time and the phase of the center frequency of the ultrasound transmitted for the second time differ from each other by 180 degrees. The ultrasound signal 60 includes a fundamental component 61, and a third-order harmonic component 62. That is, the ultrasound signal 60 is a signal having the fundamental component 61 and the third-order harmonic component 62 that have been enhanced. The ultrasound signal 60 is thus au ultrasound signal having enhanced odd-order components (odd-order harmonic components).

In response to input of the ultrasound signal 60 as input data into the trained model 170a, the trained model 170a generates an ultrasound signal 65 corresponding to the ultrasound signal 60 and outputs the ultrasound signal 65 generated, as output data. The ultrasound signal 65 is an example of a second ultrasound signal.

The ultrasound signal 65 includes a third-order harmonic component 66. The ultrasound signal 65 is a signal corresponding to target data. For example, the ultrasound signal 65 is an ultrasound signal obtained by addition of plural (three) ultrasound signals together, the plural ultrasound signals being obtained by transmission of ultrasound that is performed three times, the phases of the center frequencies of the ultrasound transmitted for the first time, the second time, and the third time differing from each other, the obtained ultrasound signal having a specific harmonic component (the third-order harmonic component 66) that has been enhanced. That is, the ultrasound signal 65 is an ultrasound signal having an enhanced harmonic component of the order that is a multiple of 3. The phase of the center frequency of the ultrasound transmitted for the first time, the phase of the center frequency of the ultrasound transmitted for the second time, and the phase of the center frequency of the ultrasound transmitted for the third time differ from each other by 120 degrees.

The ultrasound signal 65 is treated as reflected wave data. Therefore, the control circuitry 180 causes the display 103 to display a B-mode image based on the ultrasound signal 65. The B-mode image based on the ultrasound signal 65 is, for example, a B-mode image based on B-mode image data obtained from the ultrasound signal 65.

As described above, in this first embodiment, the learning device 200 generates the trained model 170a by learning using, as input data, the ultrasound signal 30 including the third-order harmonic component 32. Therefore, in making an inference, the ultrasound diagnosis apparatus 1 according to the first embodiment is able to obtain, as reflected data, the ultrasound signal 65 (output data) including the third-order harmonic component 66 that is highly accurate, by using, as input data that is input to the trained model 170a, the ultrasound signal 60 including the third-order harmonic component 62. The ultrasound signal 65 may be said to be a signal in which a fundamental component included in the ultrasound signal 60 has been suppressed and a third-order harmonic component has been maintained.

Figure 6:
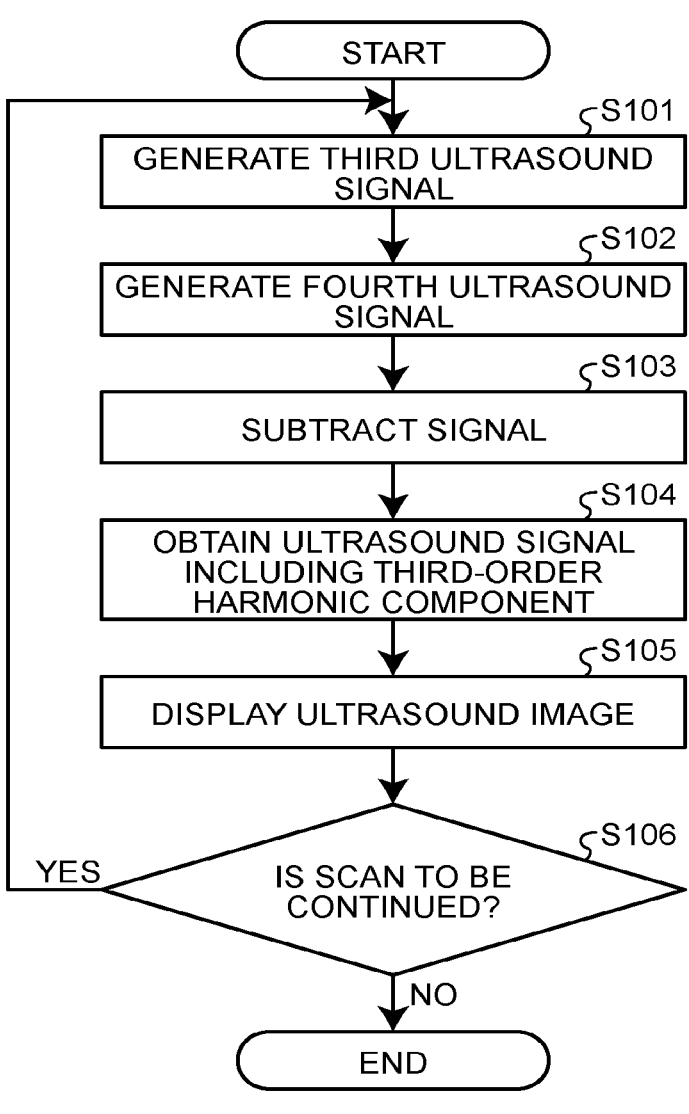
FIG. 6 is a flowchart illustrating a flow of an example of processing executed by the ultrasound diagnosis apparatus according to the first embodiment.

FIG. 6 is a flowchart illustrating a flow of an example of processing executed by the ultrasound diagnosis apparatus 1 according to the first embodiment. The processing illustrated in FIG. 6 is an example of processing in which the ultrasound diagnosis apparatus 1 generates the ultrasound signal 65 and causes the display 103 to display an ultrasound image based on the ultrasound signal 65.

As illustrated in FIG. 6, the ultrasound diagnosis apparatus 1 generates an ultrasound signal (a third ultrasound signal) similar to the ultrasound signal 20 by a method similar to the method of generating the ultrasound signal 20 (Step S101).

The ultrasound diagnosis apparatus 1 then generates an ultrasound signal (a fourth ultrasound signal) similar to the ultrasound signal 25 by a method similar to the method of generating the ultrasound signal 25 (Step S102).

The receiver circuitry 112 then generates the ultrasound signal 60 by subtracting the fourth ultrasound signal generated at Step S102 from the third ultrasound signal generated at Step S101 (Step S103).

The receiver circuitry 112 obtains, as output data, the ultrasound signal 65 including a third-order harmonic component, the ultrasound signal 65 having been output from the trained model 170a by input of the ultrasound signal 60, as input data, into the trained model 170a (Step S104).

The control circuitry 180 then causes the display 103 to display an ultrasound image (a B-mode image) based on the ultrasound signal 65 (Step S105).

The control circuitry 180 then determines whether or not scanning is to be continued (Step S106). In a case where the scanning is to be continued (Step S106: Yes), the ultrasound diagnosis apparatus 1 returns to Step S101 and executes the processing from Step S101 to Step S106 again. The processing from Step S101 to Step S106 is executed for each frame of the ultrasound image displayed on the display 103. The ultrasound image is thereby displayed as a moving image, on the display 103.

Therefore, in making an inference, for example, the trained model 170a generates the ultrasound signal 65 by executing weighted addition processing of applying a coefficient distribution to the ultrasound signal 60 input as input data, for different directions of two dimensions (a sample direction and a beam direction). The trained model 170a then outputs, as output data, the ultrasound signal 65 obtained by executing the weighted addition processing.

In a case where the scanning is not to be continued (Step S106: No), the ultrasound diagnosis apparatus 1 ends the processing illustrated in FIG. 6.

Figure 7:
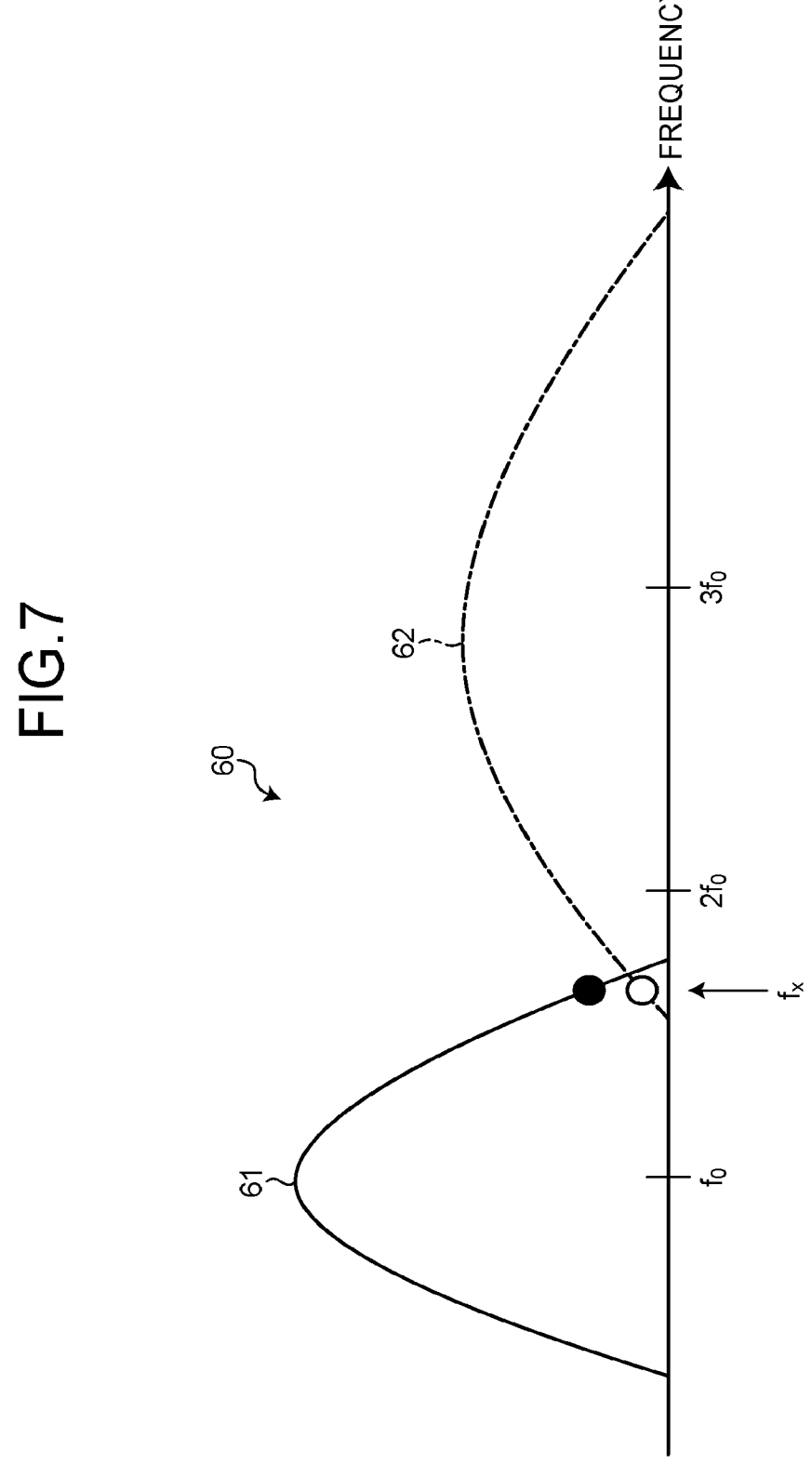
FIG. 7 is a diagram for comparison between the ultrasound diagnosis apparatus according to the first embodiment and a conventional ultrasound diagnosis apparatus.

FIG. 7 is a diagram for comparison between the ultrasound diagnosis apparatus 1 according to the first embodiment and a conventional ultrasound diagnosis apparatus. For example, in a case described below, the conventional ultrasound diagnosis apparatus suppresses the fundamental component 61 and the third-order harmonic component 62 by passing the ultrasound signal 60 through a frequency filter. In this case, a fundamental component (a fundamental component represented by a filled circle in FIG. 7) and a third-order harmonic component (a third-order harmonic component represented by an open circle in FIG. 7) are suppressed at the same proportion, the fundamental component corresponding to a frequency fx in a frequency band common between the frequency band of the fundamental component 61 and the frequency band of the third-order harmonic component 62, the third-order harmonic component corresponding to the frequency fx.

Therefore, with the conventional ultrasound diagnosis apparatus, the ratio between the fundamental component included in the ultrasound signal 60 and corresponding to the frequency fx, and the third-order harmonic component corresponding to the frequency fx, before passage of the ultrasound signal 60 through the frequency filter, does not change after the passage of the ultrasound signal 60 through the frequency filter.

By contrast, with the ultrasound diagnosis apparatus 1 according to the first embodiment, the ultrasound signal 60 includes the fundamental component 61 and the third-order harmonic component 62. However, the ultrasound signal 65 generated by the trained model 170a includes the third-order harmonic component 62 but does not include any fundamental component. Therefore, by generating the ultrasound signal 65, the ultrasound diagnosis apparatus 1 enables obtainment of an ultrasound image higher in image quality, the ultrasound image being less affected by side lobes, as compared to an ultrasound image that is based on a fundamental component. Furthermore, the ultrasound diagnosis apparatus 1 is capable of obtaining the ultrasound signal 65 while suppressing a fundamental component that is an unnecessary component and maintaining the frequency band of the third-order harmonic component 62.

As described above, at the ultrasound diagnosis apparatus 1 according to the first embodiment, the ratio between frequency components (the fundamental component and the third-order harmonic component) included in the ultrasound signal 60 and the ratio between the frequency components (the fundamental component and the third-order harmonic component) in the ultrasound signal 65 differ from each other at the specific frequency fx. That is, the ultrasound diagnosis apparatus 1 generates the ultrasound signal 65 including frequency components at a ratio different, at the specific frequency fx, from the ratio between the frequency components included in the ultrasound signal 60. Furthermore, the ultrasound diagnosis apparatus 1 generates the ultrasound signal 65 including a fundamental component and at least one harmonic component at a ratio different, at the specific frequency fx, from the ratio between the fundamental component and the at least one harmonic component that are included in the ultrasound signal 60.

Figure 8A:
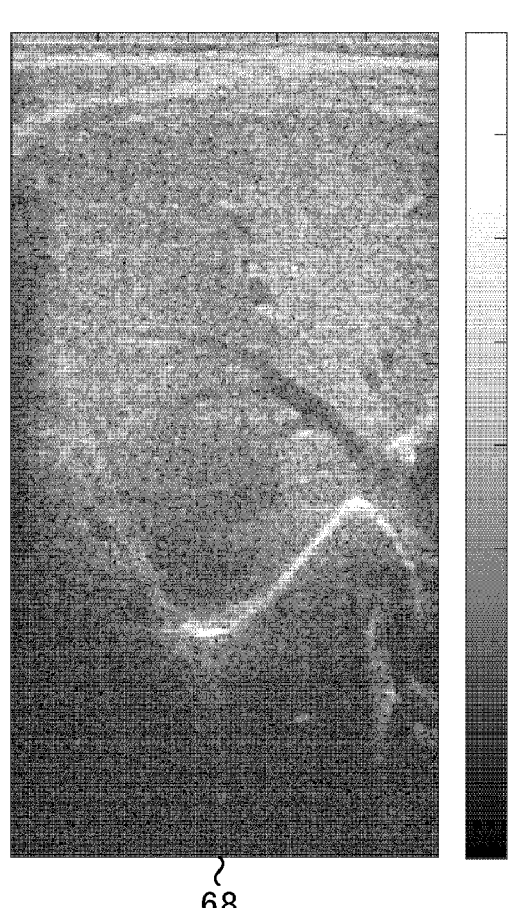
FIG. 8A is a diagram illustrating an example of an ultrasound image (a B-mode image) based on an ultrasound signal that is input data, according to the first embodiment.
Figure 8B:
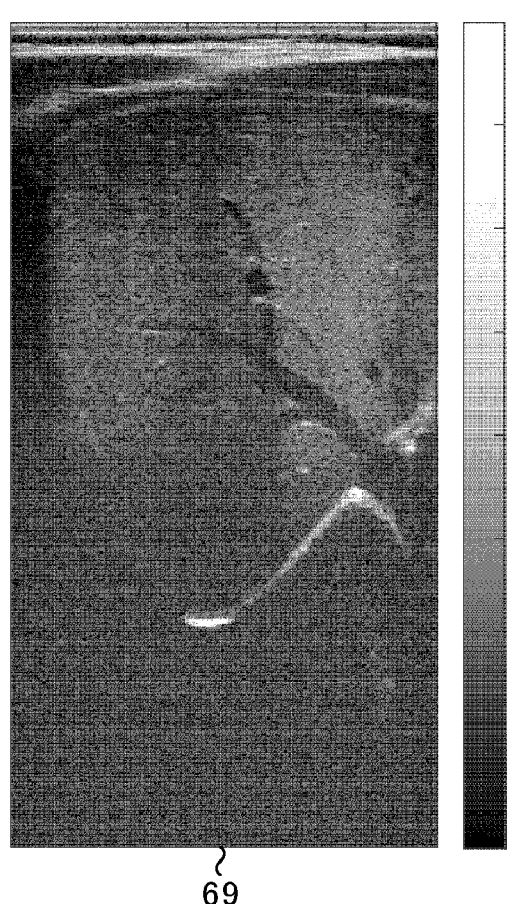
FIG. 8B is a diagram illustrating an example of an ultrasound image (a B-mode image) based on an ultrasound signal that is target data, according to the first embodiment.
Figure 8C:
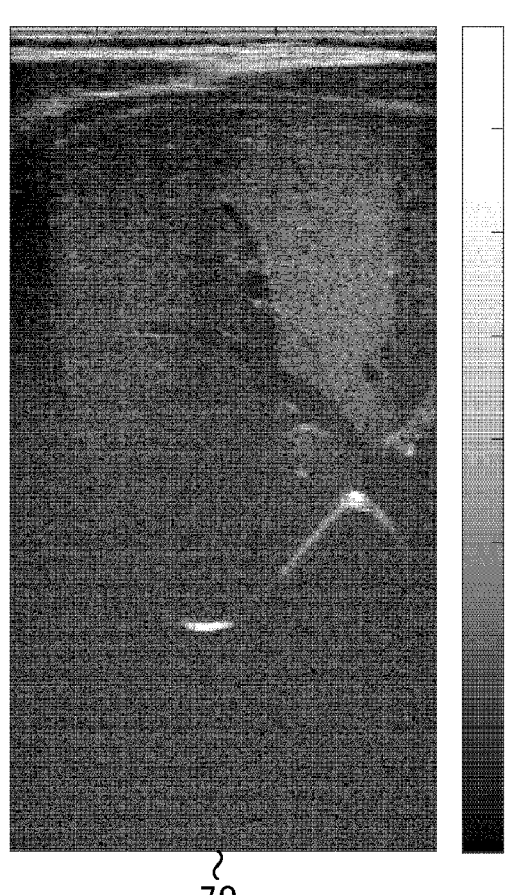
FIG. 8C is a diagram illustrating an example of an ultrasound image (a B-mode image) based on an ultrasound signal that is output data, according to the first embodiment.

FIG. 8A is a diagram illustrating an example of an ultrasound image (a B-mode image) 68 based on the ultrasound signal 60 that is input data, according to the first embodiment. FIG. 8B is a diagram illustrating an example of an ultrasound image (a B-mode image) 69 based on the ultrasound signal 55 that is target data, according to the first embodiment. FIG. 8C is a diagram illustrating an example of an ultrasound image (a B-mode image) 70 based on the ultrasound signal 65 that is output data, according to the first embodiment.

As indicated by comparison among FIG. 8A to FIG. 8C, the ultrasound image 68 includes not only a third-order harmonic component but also a fundamental component, but the ultrasound image 70 has, similarly to the ultrasound image 69, the fundamental component suppressed and the third-order harmonic component maintained.

The ultrasound diagnosis apparatus 1 according to the first embodiment has been described hereinbefore. In making an inference, the ultrasound diagnosis apparatus 1 generates the ultrasound signal 65 using the ultrasound signal 60 obtained by ultrasound transmission and reception performed twice, rather than three times. Therefore, the ultrasound diagnosis apparatus 1 according to the first embodiment enables both minimization of reduction in the frame rate and accurate obtainment of the third-order harmonic component 66.

Second Embodiment

An ultrasound diagnosis apparatus 1 according to a second embodiment will be described hereinafter. In the description of the ultrasound diagnosis apparatus 1 according to the second embodiment, description of any component similar to that of the ultrasound diagnosis apparatus 1 according to the first embodiment will be omitted, and differences from the configuration of the ultrasound diagnosis apparatus 1 according to the first embodiment will be described mainly.

In this second embodiment, it is assumed that frequencies corresponding to harmonic components of the fifth-order or higher are not included in the reception band of an ultrasound probe 101. Therefore, a reflected wave signal output from the ultrasound probe 101 includes, in addition to a fundamental component, a first-order harmonic component, a second-order harmonic component, a third-order harmonic component, and a fourth-order harmonic component, but does not include any harmonic component of the fifth order or higher.

A trained model 170a according to the second embodiment is, similarly to the trained model 170a according to the first embodiment, a machine learning model that has been trained, the machine learning model having been obtained by machine learning by a machine learning model, on the basis of input data and target data, according to a model learning program. The trained model 170a according to the second embodiment is generated by a learning device 200.

The learning device 200 generates the trained model 170a according to the second embodiment by performing learning (supervised learning) based on input data and target data related to ultrasound examination of the same position (the same cross section of the same site) of a subject. The trained model 170a has a function of outputting data (output data) corresponding to the target data in response to input of data corresponding to the input data, when making an inference. The ultrasound diagnosis apparatus 1 may include functions similar to the functions of the learning device 200 and the ultrasound diagnosis apparatus 1 may instead of the learning device 200, generate the trained model 170a.

Figure 9:
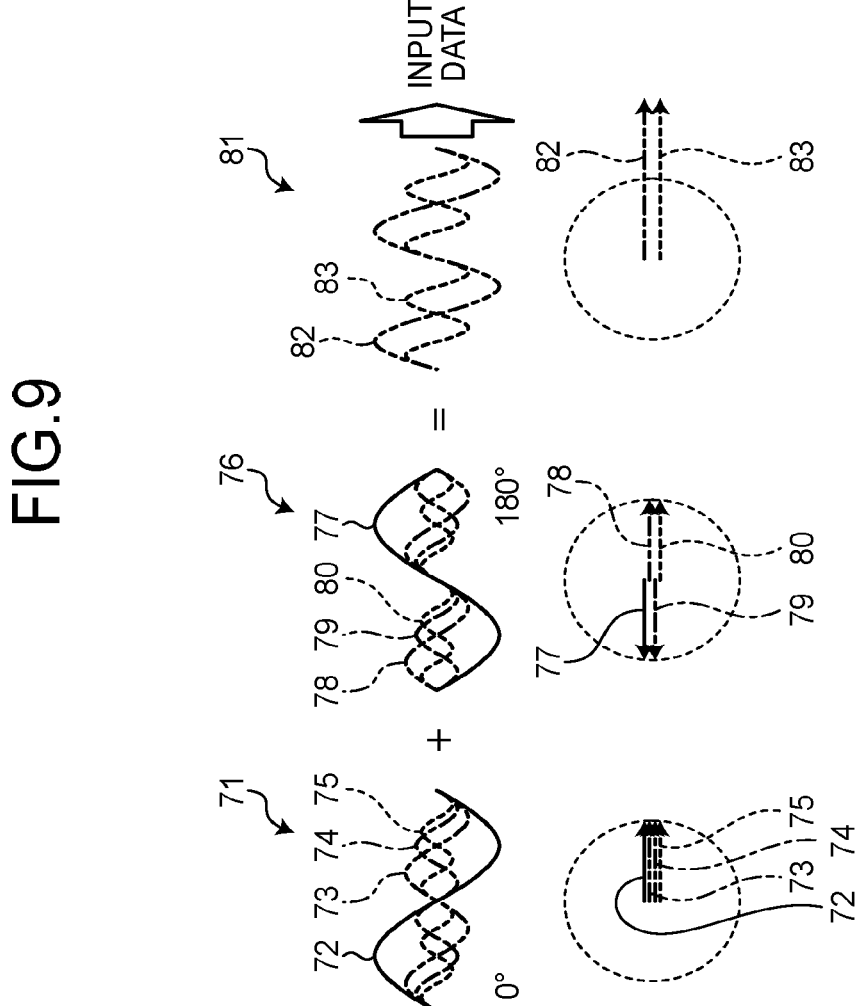
FIG. 9 is a diagram for explanation of an example of a method of generating input data, according to a second embodiment.
Figure 10:
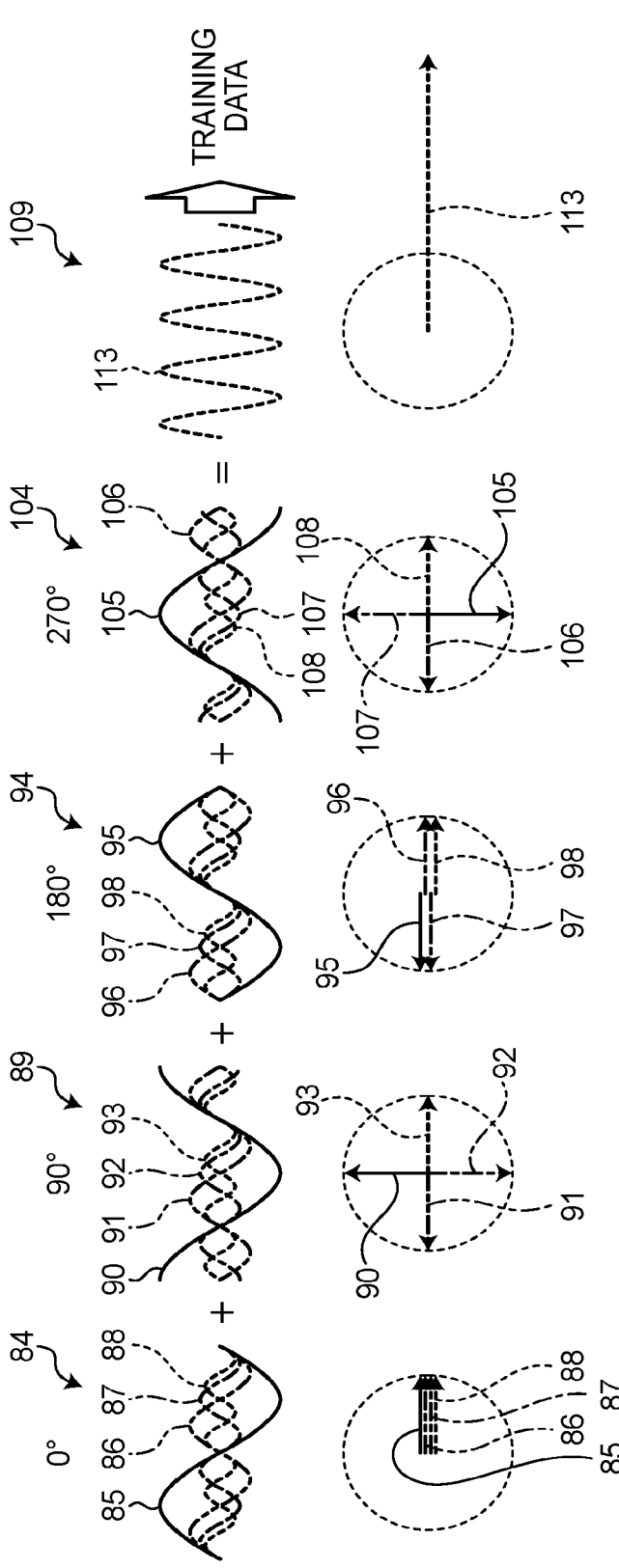
FIG. 10 is a diagram for explanation of an example of a method of generating target data, according to the second embodiment.

A method of generating input data and target data used in machine learning at the learning device 200 in this second embodiment will be described by reference to FIG. 9 and FIG. 10. FIG. 9 is a diagram for explanation of an example of a method of generating input data, according to the second embodiment. FIG. 10 is a diagram for explanation of an example of a method of generating target data, according to the second embodiment.

As illustrated in FIG. 9, the input data is an ultrasound signal 81 obtained by addition of an ultrasound signal 71 and an ultrasound signal 76 together. The ultrasound signal 71 and the ultrasound signal 76 are obtained by ultrasound transmission and reception performed twice by the ultrasound diagnosis apparatus 1. With respect to this second embodiment, a case where the ultrasound signal 71 and the ultrasound signal 76 are reflected wave data obtained by the receiver circuitry 112 will be described hereinafter.

The center frequency included in the ultrasound transmitted for the first time and the center frequency included in the ultrasound transmitted for the second time are the same. However, the phase of the center frequency included in the ultrasound transmitted for the first time and the phase of the center frequency included in the ultrasound transmitted for the second time differ from each other by 180 degrees. Furthermore, the position in the subject P, the position being where the ultrasound is transmitted to for the first time, and the position in the subject P, the position being where the ultrasound is transmitted to for the second time, are the same. That is, the scanned region in the subject P scanned by the first ultrasound transmission and reception and the scanned region in the subject P scanned by the second ultrasound transmission and reception are the same.

For example, in the first ultrasound transmission and reception, the ultrasound probe 101 transmits transmission ultrasound having a center frequency with a phase of 0 degrees, to a predetermined position in a subject P, receives reflected waves from the subject P, and transmits a reflected wave signal to an apparatus body 10. This reflected wave signal includes a harmonic component not included in the transmission ultrasound, because the subject P has non-linear characteristics.

For example, as illustrated in FIG. 9, the ultrasound signal 71 obtained by the first ultrasound transmission and reception includes a fundamental component 72, a second-order harmonic component 73, a third-order harmonic component 74, and a fourth-order harmonic component 75.

Furthermore, for example, in the second ultrasound transmission and reception, the ultrasound probe 101 transmits transmission ultrasound having a center frequency with a phase of 180 degrees, to the predetermined position in the subject P, receives reflected waves from the subject P, and transmits a reflected wave signal to the apparatus body 10.

The ultrasound signal 76 obtained by the second ultrasound transmission and reception includes a fundamental component 77, a second-order harmonic component 78, a third-order harmonic component 79, and a fourth-order harmonic component 80.

As illustrated in FIG. 9, the phase corresponding to the fundamental component 72 and the phase corresponding to the fundamental component 77 differ from each other by 180 degrees. Furthermore, the phase corresponding to the third-order harmonic component 74 and the phase corresponding to the third-order harmonic component 79 differ from each other by 180 degrees. However, the phase corresponding to the second-order harmonic component 73 and the phase corresponding to the second-order harmonic component 78 are the same. The phase corresponding to the fourth-order harmonic component 75 and the phase corresponding to the fourth-order harmonic component 80 are also the same.

Therefore, the ultrasound signal 81 includes a second-order harmonic component 82 and a fourth-order harmonic component 83, and does not include any fundamental component and third-order harmonic component. That is, the ultrasound signal 81 is a signal having a second-order harmonic component and a fourth harmonic component that have been enhanced, and a fundamental component and a third-order harmonic component in the signal have been suppressed.

The learning device 200 obtains the ultrasound signal 71 and the ultrasound signal 76 from the ultrasound diagnosis apparatus 1, adds the ultrasound signal 76 to the ultrasound signal 71 to generate the ultrasound signal 81, and uses, as input data, the ultrasound signal 81 generated. The learning device 200 may obtain the ultrasound signal 81 generated by the ultrasound diagnosis apparatus 1 and use the ultrasound signal 81 obtained, as input data.

Furthermore, as illustrated in FIG. 10, target data is an ultrasound signal 109 obtained by addition of an ultrasound signal 84, an ultrasound signal 89, an ultrasound signal 94, and an ultrasound signal 104 together. The ultrasound signal 84, the ultrasound signal 89, the ultrasound signal 94, and the ultrasound signal 104 are obtained by ultrasound transmission and reception performed four times by the ultrasound diagnosis apparatus 1. The following description is on a case where the ultrasound signal 84, the ultrasound signal 89, the ultrasound signal 94, and the ultrasound signal 104 are reflected wave data obtained by the receiver circuitry 112 in this second embodiment.

The center frequency included in the ultrasound transmitted for the first time, the center frequency included in the ultrasound transmitted for the second time, the center frequency included in the ultrasound transmitted for the third time, and the center frequency included in the ultrasound transmitted for the fourth time are the same. However, the phase of the center frequency included in the ultrasound transmitted for the first time and the phase of the center frequency included in the ultrasound transmitted for the second time differ from each other by 90 degrees. Furthermore, the phase of the center frequency included in the ultrasound transmitted for the first time and the phase of the center frequency included in the ultrasound transmitted for the third time differ from each other by 180 degrees. In addition, the phase of the center frequency included in the ultrasound transmitted for the first time and the phase of the center frequency included in the ultrasound transmitted for the fourth time differ from each other by 270 degrees.

Furthermore, the subject P to which ultrasound is transmitted for generation of input data and the subject P to which ultrasound is transmitted for generation of target data are the same. In addition, the position in the subject P where the ultrasound is transmitted to for the generation of input data and the position in the subject P where the ultrasound is transmitted to for the generation of target data are the same. That is, the scanned region in the subject P for the generation of input data and the scanned region in the subject P for the generation of target data are the same.

Furthermore, the position in the subject P where the ultrasound is transmitted to for the first time, the position in the subject P where the ultrasound is transmitted to for the second time, the position in the subject P where the ultrasound is transmitted to for the third time, and the position in the subject P where the ultrasound is transmitted to for the fourth time are the same. That is, the scanned region in the subject P scanned by the first ultrasound transmission and reception, the scanned region in the subject P scanned by the second ultrasound transmission and reception, the scanned region in the subject P scanned by the third ultrasound transmission and reception, and the scanner region in the subject P scanned by the fourth ultrasound transmission and reception are the same.

For example, in the first ultrasound transmission and reception, the ultrasound probe 101 transmits transmission ultrasound having a center frequency with a phase of 0 degrees, to a predetermined position in the subject P, receives reflected waves from the subject P, and transmits a reflected wave signal to the apparatus body 10. The ultrasound signal 84 obtained by the first ultrasound transmission and reception includes a fundamental component 85, a second-order harmonic component 86, a third-order harmonic component 87, and a fourth-order harmonic component 88.

Furthermore, for example, in the second ultrasound transmission and reception, the ultrasound probe 101 transmits transmission ultrasound having a center frequency with a phase of 90 degrees, to the predetermined position in the subject P, receives reflected waves from the subject P, and transmits a reflected wave signal to the apparatus body 10. The ultrasound signal 89 obtained by the second ultrasound transmission and reception includes a fundamental component 90, a second-order harmonic component 91, a third-order harmonic component 92, and a fourth-order harmonic component 93.

Furthermore, for example, in the third ultrasound transmission and reception, the ultrasound probe 101 transmits transmission ultrasound having a center frequency with a phase of 180 degrees, to the predetermined position in the subject P, receives reflected waves from the subject P, and transmits a reflected wave signal to the apparatus body 10. The ultrasound signal 94 obtained by the third ultrasound transmission and reception includes a fundamental component 95, a second-order harmonic component 96, a third-order harmonic component 97, and a fourth-order harmonic component 98.

Furthermore, for example, in the fourth ultrasound transmission and reception, the ultrasound probe 101 transmits transmission ultrasound having a center frequency with a phase of 270 degrees, to the predetermined position in the subject P, receives reflected waves from the subject P, and transmits a reflected wave signal to the apparatus body 10. The ultrasound signal 104 obtained by the fourth ultrasound transmission and reception includes a fundamental component 105, a second-order harmonic component 106, a third-order harmonic component 107, and a fourth-order harmonic component 108.

As illustrated in FIG. 10, the phase corresponding to the fundamental component 85 and the phase corresponding to the fundamental component 95 differ from each other by 180 degrees. Furthermore, the phase corresponding to the fundamental component 90 and the phase corresponding to the fundamental component 105 differ from each other by 180 degrees.

Furthermore, the phase corresponding to the second-order harmonic component 86 and the phase corresponding to the second-order harmonic component 91 differ from each other by 180 degrees. In addition, the phase corresponding to the second-order harmonic component 96 and the phase corresponding to the second-order harmonic component 106 differ from each other by 180 degrees.

Furthermore, the phase corresponding to the third-order harmonic component 87 and the phase corresponding to the third-order harmonic component 97 differ from each other by 180 degrees. In addition, the phase corresponding to the third-order harmonic component 92 and the phase corresponding to the third-order harmonic component 107 differ from each other by 180 degrees.

Furthermore, the phase corresponding to the fourth-order harmonic component 88, the phase corresponding to the fourth-order harmonic component 93, the phase corresponding to the fourth-order harmonic component 98, and the phase corresponding to the fourth-order harmonic component 108 are the same.

Therefore, the ultrasound signal 109 includes a fourth-order harmonic component 113 and does not include any fundamental component, second-order harmonic component, and third-order harmonic component. That is, the ultrasound signal 109 is a signal having a fourth-order harmonic component that has been enhanced, and a fundamental component, a second harmonic component, and a third-order harmonic component in the signal have been suppressed.

The learning device 200 obtains the ultrasound signal 84, the ultrasound signal 89, the ultrasound signal 94, and the ultrasound signal 104, from the ultrasound diagnosis apparatus 1, generates the ultrasound signal 109 by adding up the ultrasound signal 84, the ultrasound signal 89, the ultrasound signal 94, and the ultrasound signal 104, and uses the ultrasound signal 109 generated, as target data. The learning device 200 may obtain the ultrasound signal 109 generated by the ultrasound diagnosis apparatus 1 and use the ultrasound signal 109 obtained, as target data.

The learning device 200 generates the trained model 170a according to the second embodiment by using input data (the ultrasound signal 81) and target data (the ultrasound signal 109) that are generated by the method described above. The learning device 200 generates the trained model 170a for each site to be scanned. The ultrasound diagnosis apparatus 1 then obtains the trained model 170a generated for each site, from the learning device 200, and stores the obtained trained model 170a for each site, into a storage 170. In making an inference, the ultrasound diagnosis apparatus 1 obtains the trained model 170a corresponding to a site to be scanned, infers output data corresponding to input data by using the trained model 170a obtained, and outputs the output data inferred.

An example of operation in inference by the trained model 170a, according to the second embodiment, will be described next. The ultrasound diagnosis apparatus 1 generates, as input data to be input to the trained model 170a in making an inference, an ultrasound signal, by a method similar to the method of generating the ultrasound signal 81 illustrated in FIG. 9. This ultrasound signal generated is an example of the first ultrasound signal. Furthermore, in the following description, an ultrasound signal generated in this way may be referred to as "an ultrasound signal serving as input data for inference".

Furthermore, the receiver circuitry 112 obtains the trained model 170a corresponding to a site to be scanned, from the trained models 170a stored in the storage 170, the trained models 170a corresponding to the respective sites. The receiver circuitry 112 then inputs the ultrasound signal serving as input data for inference, into the trained model 170a. That is, in making an inference, the ultrasound diagnosis apparatus 1 performs ultrasound transmission and reception twice, the receiver circuitry 112 generates the ultrasound signal serving as input data for the inference by adding the ultrasound signal (reflected wave data) obtained by the second ultrasound transmission and reception to the ultrasound signal (reflected wave data) obtained by the first ultrasound transmission and reception.

The ultrasound signal serving as the input data for the inference includes a second-order harmonic component and a fourth-order harmonic component. That is, the ultrasound signal serving as the input data for the inference is a signal having the second-order harmonic component and the fourth-order harmonic component that have been enhanced. The ultrasound signal serving as the input data for the inference is thus an ultrasound signal having even-order harmonic components that have been enhanced.

In response to input of the ultrasound signal serving as the input data for the inference, the trained model 170a generates an ultrasound signal corresponding to the ultrasound signal serving as the input data for the inference and outputs the generated ultrasound signal as output data. This ultrasound signal output from the trained model 170a is an example of the second ultrasound signal. Furthermore, this ultrasound signal output from the trained model 170a may be referred to as "the ultrasound signal serving as output data for the inference", in the following description.

The ultrasound signal serving as the output data for the inference includes a fourth-order harmonic component. The ultrasound signal serving as the output data for the inference is a signal corresponding to target data. For example, the ultrasound signal serving as the output data for the inference is an ultrasound signal having a specific harmonic component (a fourth-order harmonic component) that has been enhanced. This specific harmonic component is obtained by addition of plural (four) ultrasound signals together. The plural ultrasound signals are obtained by transmission of ultrasound performed four times. The phases of the central frequencies of the ultrasound transmitted for the first time to the fourth time are different from each other. That is, the ultrasound signal serving as the output data for the inference is an ultrasound signal having an enhanced harmonic component of the order that is a multiple of 4.

The ultrasound signal serving as the output data for the inference is treated as reflected wave data. Therefore, the control circuitry 180 causes a B-mode image to be displayed on a display 103, the B-mode image being based on the ultrasound signal serving as the output data for the inference.

As described above, in this second embodiment, the learning device 200 generates the trained model 170a by learning using, as input data, the ultrasound signal 81 including the fourth-order harmonic component 83. Therefore, in making an inference, the ultrasound diagnosis apparatus 1 according to the second embodiment is able to accurately obtain, as reflected wave data, an ultrasound signal (an ultrasound signal serving as output data for the inference) including a fourth-order harmonic component, by using, as input data to be input to the trained model 170a, an ultrasound signal including a fourth-order harmonic component. The ultrasound signal serving as the output data for the inference may be said to be a signal having a second-order harmonic component suppressed and a fourth-order harmonic component maintained, the second-order and fourth-order harmonic components being included in the ultrasound signal serving as the input data for the inference.

The ultrasound diagnosis apparatus 1 according to the second embodiment has been described hereinbefore. In inference at the ultrasound diagnosis apparatus 1, an ultrasound signal serving as output data for the inference is generated by use of an ultrasound signal that serves as input data for the inference and that is obtained by ultrasound transmission and reception performed twice, instead of ultrasound transmission and reception performed four times. Therefore, the ultrasound diagnosis apparatus 1 according to the second embodiment enables both: minimization of reduction in the frame rate; and accurate obtainment of a fourth-order harmonic component.

Modified Examples

In the case described above with respect to the first embodiment and second embodiment, the trained model 170a executes weighted addition processing in which a coefficient distribution is applied to input data for different directions of two dimensions (the sample direction and beam direction), in making an inference. However, the trained model 170a may execute weighted addition processing in which a coefficient distribution is applied to input data for different directions of two or more dimensions (the sample direction, the beam direction, and another direction), in making an inference.

Furthermore, in the case described above with respect to the first embodiment and second embodiment, output data is obtained by addition of plural ultrasound signals together. However, output data may be an ultrasound signal obtained by subtraction of one of plural ultrasound signals from another one of the plural ultrasound signals so that the obtained ultrasound signal includes a specific harmonic component that has been enhanced.

Furthermore, in the case described above with respect to the first embodiment and second embodiment, input data, target data and output data are reflected wave data. However, the input data, the target data and the output data may be B-mode data or B-mode image data. That is, the ultrasound diagnosis apparatus 1 may use, as input data, B-mode data or B-mode image data obtained from the ultrasound signal 30, the ultrasound signal 60 or the ultrasound signal 81 by the B-mode processing circuitry 130 or image generator circuitry 150. Furthermore, the ultrasound diagnosis apparatus 1 may use, as target data, B-mode data or B-mode image data obtained from the ultrasound signal 55 or the ultrasound signal 109 by the B-mode processing circuitry 130 or image generator circuitry 150. Furthermore, the ultrasound diagnosis apparatus 1 may use, as output data, B-mode data or B-mode image data obtained from the ultrasound signal 65 by the B-mode processing circuitry 130 or image generator circuitry 150.

A program executed by a processor is provided by being incorporated in, for example, a read only memory (ROM) or a storage, beforehand. The program may be provided by being recorded in a computer-readable non-transitory recording medium, such as a compact disk (CD)-ROM, a flexible disk (FD), a CD-recordable (CD-R), or a digital versatile disk (DVD), as a file in a format that is able to be installed in or executed by the apparatuses. The program may also be provided or distributed by being stored on a computer connected to a network, such as the Internet, and being downloaded via the network. For example, the program is configured as a module or modules including the above described processing functions. As to actual hardware, by the CPU reading and executing the program from a recording medium, such as a ROM, each module is loaded and generated on a main storage.

At least one embodiment and at least one modified example described above enable both: minimization of reduction in frame rates and accurate obtainment of harmonics.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus, comprising:

an ultrasound probe, and processing circuitry that collects a first ultrasound signal including one or more harmonic components based on received signals based on reflected waves from a subject, the received signals being received by the ultrasound probe; and by executing weighed addition processing where a coefficient distribution is applied to the first ultrasound signal for different directions of two or more dimensions, generates a second ultrasound signal including components of each order at a ratio different, at a specific frequency, from a ratio among frequency components included in the first ultrasound signal, wherein the processing circuitry further collects, as the first ultrasound signal, an ultrasound signal in which a harmonic component of either an odd order or even order is enhanced relative to a harmonic component of an other order, and generates, as the second ultrasound signal, by executing the weighted addition processing on the first ultrasonic signal, a harmonic signal in which a harmonic component of a predetermined multiple order in the first ultrasound signal is enhanced more than a harmonic component of other orders in the first ultrasound signal.

2. The ultrasound diagnosis apparatus according to claim 1, wherein the processing circuitry further causes the ultrasound probe to transmit a plurality of ultrasound signals having a first phase difference to the subject, by subtracting the received signals based on the reflected waves from the subject, collects, as the first ultrasound signal, ultrasound signal in which a harmonic component of the odd order is enhanced relative to a harmonic component of the even order, and by executing the weighed addition processing on the first ultrasound signal, generates, as the second ultrasound signal, a harmonic signal in which a harmonic component of an order that is a multiple of three is enhanced more than a harmonic component of order other than the order that is the multiple of three,

the plurality of the ultrasound signals having the first phase difference is two ultrasound signals having a phase difference of 180 degrees, and the second ultrasound signal is a signal equivalent to an ultrasound signal in which a harmonic component of an order that is the multiple of three is enhanced, the signal being obtained by causing the ultrasound probe to transmit three ultrasound signals having a phase difference of 120 degrees to the subject and by adding the received signals based on the reflected waves from the subject.

3. The ultrasound diagnosis apparatus according to claim 1, wherein the processing circuitry further causes the ultrasound probe to transmit a plurality of ultrasound signals having a first phase difference to the subject, by adding the received signals based on the reflected waves from the subject, collects, as the first ultrasound signal, ultrasound signal in which a harmonic component of the even order is enhanced relative to a harmonic component of the odd order, and by executing the weighed addition processing on the first ultrasound signal, generates, as the second ultrasound signal, a harmonic signal in which a harmonic component of an order that is a multiple of four is enhanced more than a harmonic component of order other than the order that is the multiple of four, the plurality of the ultrasound signals having the first phase difference is two ultrasound signals having a phase difference of 180 degrees, and the second ultrasound signal is a signal equivalent to an ultrasound signal in which a harmonic component of an order that is the multiple of four is enhanced, the signal being obtained by causing the ultrasound probe to transmit four ultrasound signals having a phase difference of 90 degrees to the subject and by adding the received signals based on the reflected waves from the subject.

4. The ultrasound diagnosis apparatus according to claim 2, wherein the processing circuitry further generates the second ultrasound signal by using a trained model that is trained to output a harmonic signal in which a harmonic component of an order that is a multiple of three is enhanced more than a harmonic component of order other than the order that is the multiple of three, in response to input of an ultrasonic signal in which a harmonic component of the odd order is enhanced relative to a harmonic component of the even order.

5. The ultrasound diagnosis apparatus according to claim 3, wherein the processing circuitry further generates the second ultrasound signal by using a trained model that is trained to output a harmonic signal in which a harmonic component of an order that is a multiple of four is enhanced more than a harmonic component of order other than the order that is the multiple of four, in response to input of an ultrasonic signal in which a harmonic component of the even order is enhanced relative to a harmonic component of the odd order.

6. A harmonic signal obtaining method, comprising:

collecting a first ultrasound signal including one or more harmonic components based on received signals based on reflected waves from a subject, the received signals being received by an ultrasound probe; and by executing weighed addition processing where a coefficient distribution is applied to the first ultrasound signal for different directions of two or more dimensions, generating a second ultrasound signal including components of each order at a ratio different, at a specific frequency, from a ratio among frequency components included in the first ultrasound signal, wherein the collecting further comprises collecting, as the first ultrasound signal, ultrasound signal in which a harmonic component of either an odd order or even order is enhanced relative to a harmonic component of the other order, and the generating further comprises generating, as the second ultrasound signal, by executing the weighted addition processing on the first ultrasonic signal, a harmonic signal in which a harmonic component of a predetermined multiple order in the first ultrasound signal is enhanced more than harmonic component of other orders in the first ultrasound signal.

* * * * *